(12) United States Patent
Laborie et al.

(10) Patent No.: US 6,679,975 B2
(45) Date of Patent: Jan. 20, 2004

(54) PROCESS FOR RECOVERING THE METHANOL CONTAINED IN A LIQUID HYDROCARBON FEED

(75) Inventors: Géraldine Laborie, Courbevoie (FR); Fabrice Lecomte, Rueil Malmaison (FR); Annick Pucci, Croissy sur Seine (FR)

(73) Assignee: Institut Francais du Petrole, Rueil Malmaison cedex (FR)

( * ) Notice: Subject to any disclaimer, the term of this patent is extended or adjusted under 35 U.S.C. 154(b) by 0 days.

(21) Appl. No.: 10/036,416

(22) Filed: Jan. 7, 2002

(65) Prior Publication Data

US 2002/0088704 A1 Jul. 11, 2002

(30) Foreign Application Priority Data

Jan. 9, 2001 (FR) .......................................... 01 00283

(51) Int. Cl.[7] .......................... B01D 3/36; C07C 31/04; C07C 29/82
(52) U.S. Cl. ................... 203/66; 203/78; 203/DIG. 23; 203/43; 203/70; 208/348; 568/902.2; 568/913; 95/158
(58) Field of Search .............................. 202/185.2, 204; 210/673; 568/902.2, 913; 203/50, 66, 95, 18, 78, 70, DIG. 23, 43, 42; 62/50.1; 95/158, 179; 208/348; 44/451

(56) References Cited

U.S. PATENT DOCUMENTS

| | | | | |
|---|---|---|---|---|
| 1,372,465 A | * | 3/1921 | Stevens .................. | 203/19 |
| 2,428,467 A | * | 10/1947 | Petry et al. .............. | 203/66 |
| 2,618,591 A | * | 11/1952 | Anderson ................ | 203/66 |
| 3,284,348 A | * | 11/1966 | Hutton ................... | 208/348 |
| 3,293,154 A | * | 12/1966 | Newton ................... | 203/18 |
| 4,014,667 A | | 3/1977 | Barber ..................... | 55/32 |
| 4,243,493 A | * | 1/1981 | Gruber et al. ............ | 203/66 |
| 4,302,298 A | * | 11/1981 | Mikitenko et al. ........ | 203/75 |

FOREIGN PATENT DOCUMENTS

| | | | | |
|---|---|---|---|---|
| FR | 2 605 241 | 10/1986 | .......... | B01D/53/26 |
| FR | 2 636 857 | 9/1988 | .......... | B01D/53/14 |

OTHER PUBLICATIONS

French Search Report w/English translation.

\* cited by examiner

*Primary Examiner*—Virginia Manoharan
(74) *Attorney, Agent, or Firm*—Antonelli, Terry, Stout & Kraus, LLP

(57) ABSTRACT

The present invention aims to isolate the azeotropes formed in a distillation column (B1) by methanol, propane and butane. The azeotropes are then liquefied in heat exchanger (E2) and mixed in contactor (M1) with water in order to dissolve the methanol in water. The mixture is then fed into a decantation tank (D2) to separate the aqueous phase from the liquid hydrocarbon phase. Finally, an aqueous phase containing methanol is discharged and the methanol-depleted hydrocarbon phase is recycled to distillation column (B1) as reflux.

9 Claims, 2 Drawing Sheets

PROCESS FOR RECOVERING THE METHANOL CONTAINED IN A LIQUID HYDROCARBON FEED

FIELD OF THE INVENTION

The object of the present invention is a process for recovering the methanol contained in a liquid hydrocarbon feed.

BACKGROUND OF THE INVENTION

Patents FR-B-2,605,241 and FR-B-2,636,857 relate to a natural gas treating process allowing to achieve at least dehydration and recovery of the natural gas liquids contained in the gas by temperature lowering. The gas is protected against hydrates formation by addition of methanol. At the end of the cooling stage, three phases are separated in a decantation drum (an aqueous liquid phase, a hydrocarbon liquid phase referred to as <<natural gas liquids>> or <<NGL>> and a gas phase consisting of methane), these three phases containing methanol.

For economic reasons, it is advantageous to recover the methanol contained in the hydrocarbon liquid phase.

U.S. Pat. No. 4,014,667 describes a process for recovering the methanol present in a hydrocarbon liquid phase. This process consists in water washing the hydrocarbon liquid phase and it is carried out in a liquid/liquid contacting device, a mixer/contactor for example. After contacting, the hydrocarbon liquid phase is free from almost all of the methanol and it is subjected to a separation operation for separating the hydrocarbons that constitute it. The separation operation can be carried out in a distillation column arranged downstream from the liquid/liquid contacting device.

This water washing process is advantageous in that it is relatively simple, it does not require high installation and operating costs, and it allows to recover a great fraction of the methanol present in the hydrocarbon liquid phase.

However, the process according to patent U.S. Pat. No. 4,014,667 has certain drawbacks. At the outlet of the mixer/decanter, the hydrocarbon liquid phase is water saturated and it has to be subjected to an additional dehydration stage.

Furthermore, liquid/liquid contacting of the hydrocarbon liquid phase with water, downstream from the distillation column, presents at least two drawbacks. On the one hand, contacting can cause cooling of the hydrocarbon phase before it is fed into the distillation column, which requires a higher energy supply in the distillation column to separate the hydrocarbons. On the other hand, during contacting, the hydrocarbon phase fills with water, which increases the amount of material to be processed in the distillation column.

Besides, this water washing process allows to recover only an aqueous solution with a low methanol concentration. It is then necessary to use a fractionating column to separate the methanol from the wash water.

The invention proposes a new process for recovering the methanol contained in a hydrocarbon liquid phase. This process can be applied for processing the natural gas liquids obtained with the processes described in patents FR-B-2,605,241 and FR-B-2,636,857. This new process allows to overcome the aforementioned drawbacks.

SUMMARY OF THE INVENTION

The present invention uses the fact that methanol forms azeotropes with propane and butane. The boiling temperature of methanol-propane and methanol-butane azeotropes is lower than that of the propane and butane pure substances and substantially different from that of the other alkanes. It is thus possible to separate by distillation the methanol azeotropes from the other hydrocarbons and notably from propane and butane. The methanol can thus be isolated in a small stream of matter in relation to the stream to be treated.

The present invention aims to isolate the azeotropes formed in a distillation column by methanol, propane and butane. The azeotropes are then liquefied and mixed with water so as to dissolve the methanol in the water. Then the mixture is fed into a decantation tank to separate the aqueous phase from the liquid hydrocarbon phase. Finally, a methanol-containing aqueous phase is discharged and the methanol-depleted hydrocarbon phase is recycled to the distillation column as reflux.

The process according to the invention can be generally defined as a process for recovering the methanol contained in a hydrocarbon liquid feed, comprising the following stages:

a) distilling the hydrocarbon liquid phase containing the methanol to isolate a gas phase consisting of methanol-hydrocarbons azeotropes, b) mixing said gas phase obtained in stage a) with water, c) separating the mixture obtained in stage b) into a methanol-rich aqueous phase and a methanol-poor hydrocarbon phase, said hydrocarbon phase being recycled to stage a).

According to the process of the invention, the azeotropes isolated can be methanol-propane and methanol-butane. Said gas phase obtained in stage a) can be either liquefied before stage b), or said gas phase can be liquefied upon mixing with the water during stage b). In stage c), the mixture obtained in stage b) can be separated by decantation. Before stage a), the methane and the ethane can be separated from the hydrocarbon liquid phase by distillation. In stage a), a liquid phase containing the hydrocarbons consisting of more than five carbon atoms and a gas phase containing propane and butane can be obtained.

The process according to the invention can be used to process the methanol-containing hydrocarbon liquid phase obtained after dehydration or dehydration and deacidizing of a raw natural gas.

The process according to the invention, wherein the methanol-rich aqueous phase obtained in stage c) is recycled, can be used in a raw natural gas dehydration or dehydration and deacidizing process.

The process according to the invention affords many advantages in relation to the prior art.

The process according to the invention allows to make significant energy savings. Since no water washing is performed upstream from the hydrocarbon separation column, the hydrocarbon liquid phase is neither cooled nor water saturated. Thus, the distillation column processes a low-flow rate and warmer stream, and it therefore requires less heat for separation of the hydrocarbons and of the azeotropes. Furthermore, according to the process of the invention, mixing of the azeotropes obtained at the top of the distillation column with water allows to reduce the temperature of said azeotropes or even to liquefy them.

Besides, the process according to the invention requires a lower stream of water than the washing process according to the prior art. According to the invention, this water stream is under no obligation to dissolve all of the methanol contained in the azeotropic mixture. In fact, the hydrocarbon liquid phase obtained after mixing with the water is recycled in the process as reflux to the distillation column. A concentration of 10% by mole of methanol in the aqueous phase discharged can thus be obtained.

BRIEF DESCRIPTION OF THE FIGURES

Other features and advantages of the invention will be clear from reading the description hereafter, given by way of non limitative example, with reference to the accompanying drawings wherein.

DETAILED DESCRIPTION

Figure 1:
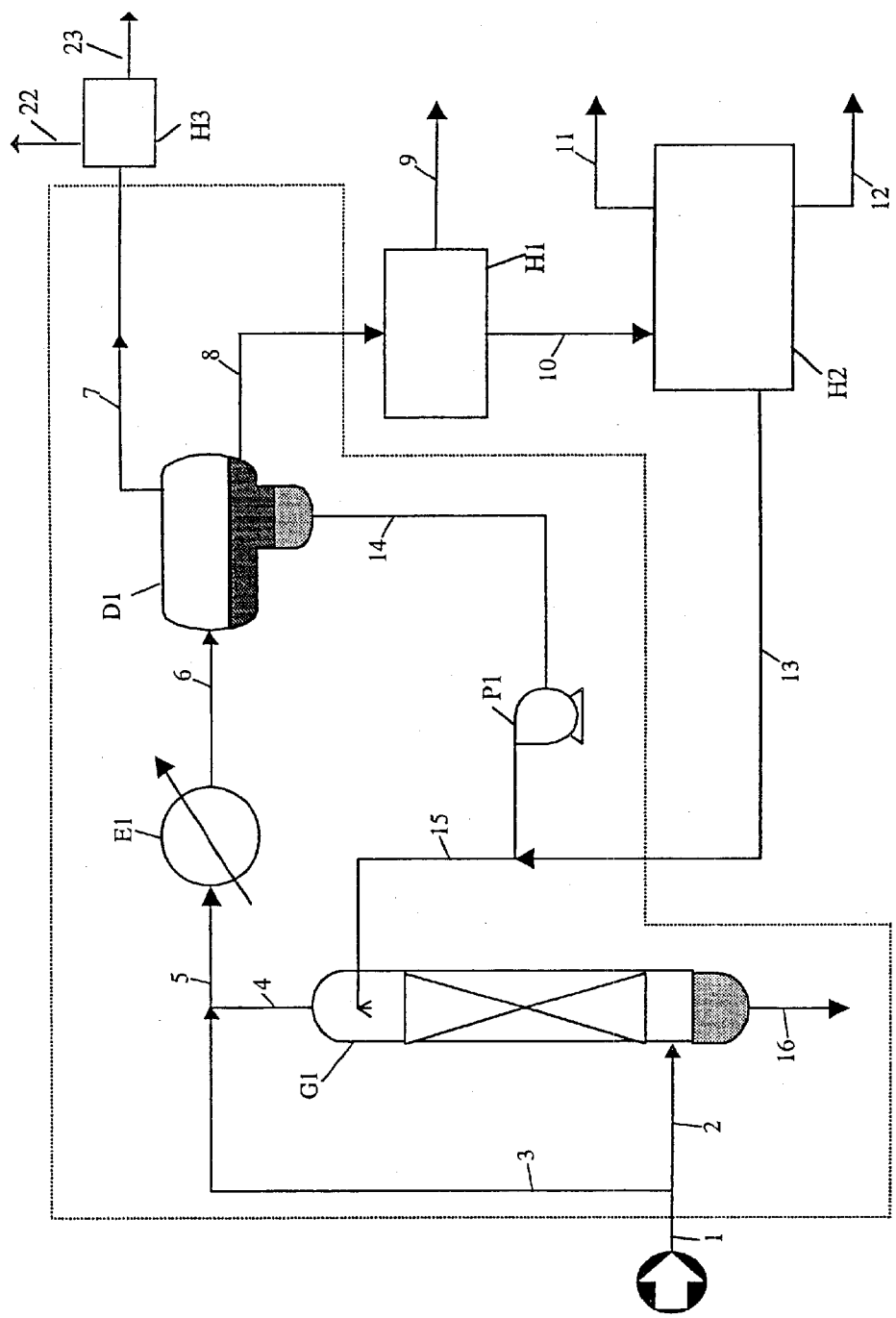
FIG. 1 diagrammatically shows the process of the invention combined with a natural gas dehydration and stripping process, FIG. 2 diagrammatically shows an embodiment of the process according to the invention.

In FIG. 1, the methanol recovery process according to the invention, diagrammatically shown by symbols H1 and H2, is arranged behind a dehydration and stripping process as described in patent FR-B-2,605,241. This dehydration and stripping process is diagrammatically shown in FIG. 1 by the symbols contained in the space surrounded by a dotted line. The process described in patent FR-B-2,636,857 takes up the process of patent FR-B-2,605,241 and adds thereto a deacidizing stage shown in FIG. 1 by symbol H3.

With reference to FIG. 1, the raw natural gas to be processed flows in through line 1. A fraction of the gas to be processed is fed, through line 2, into contact zone G1 consisting for example of a packing. The gas is brought into countercurrent contact with a liquid phase consisting of methanol and of water, fed into contact zone G1 through line 15.

The natural gas discharged at the top of contact zone G1 contains steam and methanol, most often in amounts close to saturation. This gas is collected in line 4 and mixed with the remaining fraction of raw natural gas coming from line 1 through line 3. An aqueous fraction decants at the bottom of contact zone G1 and it is discharged through line 16.

The mixture conveyed through line 5 is then cooled in a heat exchanger E1 by a coolant. The cooling stage carried out in exchanger E1 allows to condense a fraction of the hydrocarbons whose molecular mass is greater than or equal to that of ethane. It also allows to condense the major part of the water and of the methanol that were contained in the gas fed into exchanger E1.

The fluid consisting of condensate and gas at the outlet of exchanger E1 is sent to a decantation zone D1 through line 6. Three phases are separated in decantation zone D1: a methanol-containing aqueous phase, a hydrocarbon liquid phase corresponding to alkanes whose molecular mass is greater than or equal to that of ethane, and a gas phase corresponding to the methane of the dehydrated natural gas. The dehydrated methane is discharged from decantation zone D1 through line 7. The methanol-containing aqueous phase is discharged through line 14, then sent to contact zone G1 by means of pump P1 and line 15.

According to the process described in patent FR-B-2,636,857, the dehydrated methane is sent through line 7 to a deacidizing device H3. At the end of the deacidizing process carried out in device H3, a gaseous stream consisting of dehydrated methane and freed from acid gases is discharged through line 22 while the acid gases are discharged through line 23.

Figure 2:
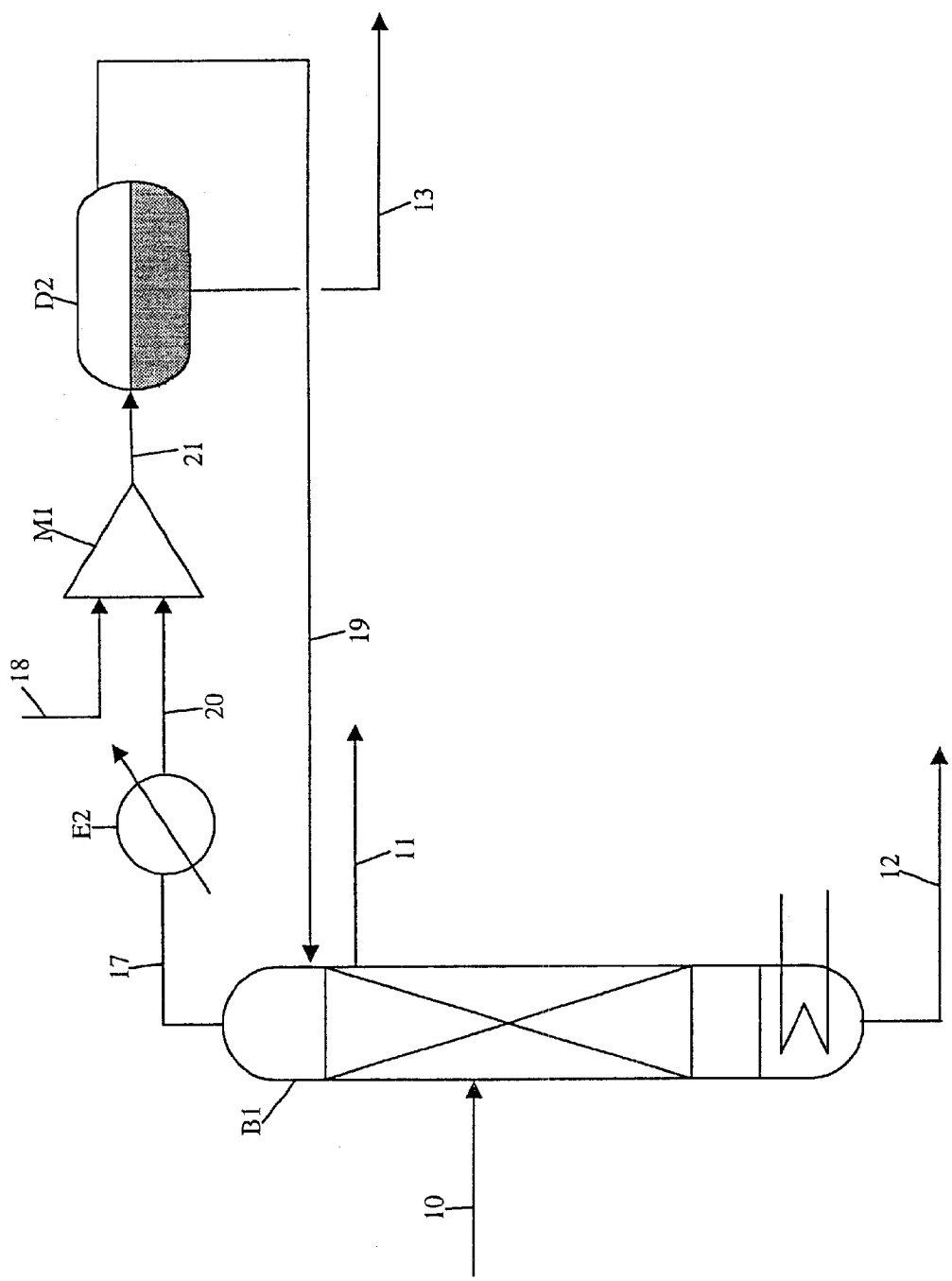

The hydrocarbon liquid phase separated in decantation zone D1 constitutes the feed to be treated by means of the process according to the present invention. The process is represented in FIG. 1 by symbols H1 and H2. FIG. 2 shows in detail the process represented by symbol H2 in FIG. 1.

The hydrocarbon liquid phase is sent through line 8 to a deethanizer H1 in order to remove the methane and the ethane still present in the liquid phase. Deethanizer H1 can consist of a distillation column known to the man skilled in the art. The methane and the ethane are discharged through line 9.

With reference to FIG. 2, the hydrocarbon liquid phase to be processed, recovered at the outlet of deethanizer H1 through line 10, contains propane, butane, i-butane, n-butane, i-pentane, n-pentane, hexane and heptane, as well as methanol It is sent through line 10 to a distillation column B1 so as to fractionate and to recover a gas phase of methanol-propane and methanol-butane azeotropes formed in said column B1, a propane/butane gas cut and a liquid hydrocarbon cut, mainly consisting of at least five carbon atoms, commonly referred to as natural gasoline. Column B1 receives as reflux a liquid phase consisting of propane, butane and methanol through line 19.

At the bottom of column B1, a liquid hydrocarbon phase corresponding to the natural gasoline is discharged through line 12. At an intermediate level, between the bottom and the top of the column, where suitable thermodynamic conditions prevail, the pure propane/butane cut is discharged through line 11. At the top of column B1, a gas phase containing the methanol-propane and methanol-butane azeotropes formed during distillation is discharged through line 17.

The gas phase recovered at the top of column B1 through line 17 is cooled in a heat exchanger E2 in order to cause complete condensation of the azeotropes. The liquid phase coming from exchanger E2 through line 20 is contacted in contact zone M1 with a stream of water flowing in through line 18. The mixture obtained in contact zone M1 is sent to decantation tank D2 through line 21.

The condensation operation in heat exchanger E2 is not necessary if the water stream flowing into contact zone Ml is cold and great enough to liquefy the azeotropes by simple gas/liquid contact.

Two liquid phases are separated in decantation tank D2, a hydrocarbon phase containing propane, butane and a small fraction of methanol, and a methanol-rich aqueous phase. The aqueous phase is discharged from the device through line 13. This aqueous phase can be recycled in the process according to patent FR-B-2,605,241 or patent FR-B-2,636,857 through lines 13 and 15 to contact zone G1. The hydrocarbon phase is recycled as reflux to the top of distillation column B1 by means of line 19.

The description hereafter is an example of implementation of the process according to the invention described in connection with FIGS. 1 and 2. This description, given by way of example, does not limit in any way the scope of the invention.

A liquid hydrocarbon feed containing 48.6% by mole of propane, 14.9% n-butane, 13.9% i-butane, 5.6% n-pentane, 5.6% i-pentane, 4.1% hexane, 6.3% heptane and 0.9% methanol is processed at the outlet of a deethanizer H1 downstream from the dehydration and stripping process carried out according to patent FR-B-2,605,241 or patent FR-B-2,636,857. The feed comes from the bottom of the deethanizer through line 10, at a temperature of 75° C. and a pressure of 17 bars. The flow rate of the feed is 1824.64 kmol/h.

After compression to 20 bars, the feed is introduced into column B1 in order to be fractionated into a propane/butane cut and a cut containing the hydrocarbons mainly consisting of more than five carbon atoms. Column B1 is a distillation column comprising 40 theoretical plates and working under a pressure of 20 bars. The column is fed through line 10 at the level of the twentieth plate. In column B1, the methanol-propane and methanol-butane azeotropes form and flow to the top of the distillation column.

The gas phase consisting of the azeotropes flows out of column B1 through line 17, it is cooled in exchanger E2 to a temperature of 62° C., which causes total condensation. The liquid recovered at the outlet of condenser E2 is mixed with water in a mixer M1 in order to dissolve the methanol in the water. Mixer M1 can be a device marketed by the Sulzer company. The flow rate of the water introduced at the level of line 18 is 75 kmol/h.

The mixture thus formed is sent to separator D2 where two liquid phases are separated: an aqueous phase containing a methanol fraction and a hydrocarbon phase with methanol traces. The aqueous phase is discharged from the system by means of line 13; its flow rate is 82.9 kmol/h and it contains 9.5% by mole of methanol. The aqueous phase is recycled in the dehydration and stripping process according to patent FR-B-2,605,241 or patent FR-B-2,636,857 (see FIG. 1) to the top of column G1. The total amount of methanol recovered is 50%. The hydrocarbon phase is sent back to distillation column B1 through line 19. The flow rate of this stream is 2822 kmol/h.

The propane/butane cut is discharged at the level of the second plate of column B1 by means of line 11. The discharge rate is 1415 kmol/h so as to have a reflux ratio of 2 at the level of column B1. This reflux ratio is a compromise between the total amount of methanol recovered and the concentration of methanol in the aqueous phase discharged through line 15. The cut contains 62.7% propane, 17.9% i-butane and 18.8% n-butane.

The cut corresponding to the heavier hydrocarbons, mainly comprising at least five carbon atoms, is discharged at the bottom of column B1 through line 12.

What is claimed is:

1. A process for recovering methanol contained in a liquid hydrocarbon feed, comprising the following stages:

a) distilling the liquid hydrocarbon feed containing the methanol so as to isolate a gas phase consisting essentially of methanol-propane and methanol-butane, b) mixing said gas phase obtained in stage a) with water, c) separating the mixture obtained in stage b) into a methanol-rich aqueous phase and a methanol-poor hydrocarbon phase, said hydrocarbon phase being recycled to stage a).

2. A process as claimed in claim 1, wherein, before stage b), said gas phase obtained in stage a) is liquefied.

3. A process as claimed in claim 2, wherein, in stage c), the mixture obtained in stage b) is separated by decantation.

4. A process as claimed in claim 1, wherein, in stage b), said gas phase is liquefied during mixing with the water.

5. A process as claimed in claim 1, wherein, before stage a), methane and ethane are separated from the liquid hydrocarbon feed by distillation.

6. A process as claimed in claim 5, wherein, in stage a), a liquid phase containing hydrocarbons having more than five carbon atoms and a second gas phase containing propane and butane are further obtained.

7. A process as claimed in claim 1, further comprising obtaining the liquid hydrocarbon feed containing methanol from a raw natural gas dehydration process.

8. A process as claimed in claim 7, wherein the methanol-rich aqueous phase obtained in stage c) is recycled to the raw natural gas dehydration and deacidizing process.

9. A process as claimed in claim 1, further comprising obtaining the liquid hydrocarbon feed containing methanol from a raw natural gas dehydration and deacidizing process.

* * * * *